US00PP13975P29

(12) United States Plant Patent
Hansen

(10) Patent No.: US PP13,975 P2
(45) Date of Patent: Jul. 15, 2003

(54) CLEMATIS PLANT NAMED 'PRINSESSE ALEXANDRA'

(75) Inventor: Flemming Hansen, Rønde (DK)

(73) Assignee: Future Plants V.O.F., Lisserbroek (NL)

( * ) Notice: Subject to any disclaimer, the term of this patent is extended or adjusted under 35 U.S.C. 154(b) by 0 days.

(21) Appl. No.: 10/139,954

(22) Filed: May 6, 2002

(51) Int. Cl.[7] ..... A01H 5/00

(52) U.S. Cl. ..... Plt./228

(58) Field of Search ..... Plt./228

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Clematis plant named 'Prinsesse Alexandra', characterized by its upright growth habit; freely branching habit; freely flowering habit; and large single and semi-double flowers that are pink in color.

1 Drawing Sheet

BOTANICAL CLASSIFICATION/CULTIVAR DESIGNATION

*Clematis L.* cultivar Prinsesse Alexandra.

BACKGROUND OF THE INVENTION

The present Invention relates to a new and distinct cultivar of Clematis plant, botanically known as *Clematis L.,* and hereinafter referred to by the name 'Prinsesse Alexandra'.

The new cultivar originated from a random cross-pollination of two unidentified selections of *Clematis L.,* not patented, in Ronde, Denmark. The new cultivar was discovered and selected by the Inventor as a flowering plant within the progeny from this cross-pollination in a controlled environment in Ronde, Denmark, in 1998.

Asexual reproduction of the new cultivar by cuttings taken in Ronde, Denmark, since 1999, has shown that the unique features of this new Clematis are stable and reproduced true to type in successive generations.

SUMMARY OF THE INVENTION

Plants of the cultivar Prinsesse Alexandra have not been observed under all possible environmental conditions. The phenotype may vary somewhat with variations in environment such as temperature and light intensity without, however, any variance in genotype.

The following traits have been repeatedly observed and are determined to be the unique characteristics of 'Prinsesse Alexandra'. These characteristics in combination distinguish 'Prinsesse Alexandra' as a new and distinct cultivar of Clematis:

1. Upright growth habit.
2. Freely branching habit.
3. Freely flowering habit.
4. Large single and semi-double flowers that are pink in color.

Plants of the new Clematis differ primarily from plants of the unidentified parent selections primarily in flower form and flower color.

Plants of the new Clematis can be compared to plants of the *Clematis L.* cultivar Nelly Moser, not patented. In side-by-side comparisons conducted in Ronde, Denmark, plants of the new Clematis differed from of the cultivar Nelly Moser in the following characteristics:

1. Plants of the new Clematis had single and double flowers whereas plants of the cultivar Nelly Moser had single flowers.

2. Plants of the new Clematis had larger flowers than plants of the cultivar Nelly Moser.

3. Single flowers of plants of the new Clematis had yellow-colored centers whereas flowers of plants of the cultivar Nelly Moser had white-colored centers.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Clematis. The photograph comprises a side perspective view of typical flowering plants of 'Prinsesse Alexandra'.

DETAILED BOTANICAL DESCRIPTION

In the following description, color references are made to The Royal Horticultural Society Colour Chart, 2001 Edition, except where general terms of ordinary dictionary significance are used. Plants used for the photograph and the following description were about two years old and were grown in containers in an outdoor nursery in Ronde, Denmark. The following measurements and values represent averages taken from a group of typical flowering plants during the late summer.

Botanical classification: *Clematis L.* cultivar Prinsesse Alexandra.

Parentage:

*Female, or seed, parent.*—Unidentified selection of *Clematis L.,* not patented.

*Male, or pollen, parent.*—Unidentified selection of *Clematis L.,* not patented.

Propagation:

*Type.*—By cuttings.

*Time to initiate roots.*—About 20 to 30 days at 18° C.

*Time to produce a rooted young plant.*—About 100 days at 22° C.

*Root description.*—Numerous, fleshy.

Plant description:

*Form.*—Perennial flowering vine; upright, broadly conical. Plants are freely branching with typically about 12 lateral branches per plant; pinching is typically not necessary. Vigorous growth habit.

*Plant height* (*length*).—About 2 meters.

*Plant diameter.*—About 1 meter.

*Lateral branches.*—Length: About 1 meter. Diameter: About 5 mm. Internode length: About 15 cm. Shape: Round to somewhat flattened in cross-section. Strength: Flexible, strong. Texture: Sparsely pubescent. Color: Young stems: 144A to 144B. Mature stems: 197A.

*Foliage description.*—Arrangement: Opposite; compound; three leaflets per leaf. Length, leaflet: About 9 cm. Length, leaf: About 26 cm. Width, leaflet: About 5.5 cm. Width, leaf: About 20 cm. Shape, leaflet: Ovate. Apex, leaflet: Apiculate. Base, leaflet: Obtuse to somewhat attenuate. Margin, leaflet: Entire. Texture, leaflet: Upper surface: Very short hairs along primary veins; leathery. Lower surface: Sparsely pubescent; leathery. Venation pattern. leaflet: Pinnate. Petiole length. leaflet: About 9 mm. Petiole diameter, leaflet: About 2 mm. Color, leaflet: Developing leaves, upper surface: 137A. Developing leaves, lower surface: 137A to 137B. Fully expanded leaves, upper surface: 139A. Fully expanded leaves, lower surface: 137A to 137B. Venation, upper surface: 139A. Venation, lower surface: 137A to 137B. Petiole: 144A.

Flower description:

*Flower type and habit.*—Single and semi-double flowers arranged singly at lateral branch terminals; about 50 flowers per plant will develop during the flowering season. Flowers face upright to somewhat outward. Flowers not persistent.

*Natural flowering season.*—Flowering continuous from the end of May until September in Ronde, Denmark.

*Flower longevity on the plant.*—About one week.

*Fragrance.*—None detected.

*Flower shape, single flowers.*—Rotate, flat.

*Flower shape, semi-double flowers.*—Rotate, slightly globular.

*Flower diameter, single flowers.*—About 15 cm.

*Flower diameter, semi-double flowers.*—About 10 cm.

*Flower depth* (*height*), *single flowers.*—About 1.8 cm.

*Flower depth* (*height*), *semi-double flowers.*—About 2.2 cm.

*Flower buds.*—Length: About 3 cm. Diameter: About 1.2 cm. Shape: Ovoid. Color: 138B to 138C.

*Petals.*—None observed.

*Sepals.*—Quantity per flower, single flowers: About seven. Quantity per flower, semi-double flowers: About 50. Length, single flowers: About 6.7 cm. Length, semi-double flowers: About 5 cm. Width, single flowers: About 3.4 cm. Width, semi-double flowers: About 2.7 cm. Shape, single and semi-double flowers: Elliptic to broadly oblanceolate. Apex, single flowers: Mucronate. Apex, semi-double flowers: Aristate, short. Base, single and semi-double flowers: Attenuate. Margin, single and semi-double flowers: Entire; undulate. Texture, single and semi-double flowers, upper surface: Glabrous, smooth. Texture, single and semi-double flowers, lower surface: Sparsely pubescent. Color, single flowers: When and fully opened, upper surface: 65D; broad central longitudinal stripe, 77C to 84B; broad central stripe fading to 76C with subsequent development. When and fully opened, lower surface: 76B to 76C; central longitudinal stripe, 145C to 145D to 149D. Color, semi-double flowers: When and fully opened, upper surface: 65D to 69C; broad central longitudinal stripe, slightly darker than 69C. When and fully opened, lower surface: 70C to 70D with greenish, 189C, tints; central longitudinal stripe, 145C to 145D to 149D.

*Peduncles.*—Length: About 10 cm. Diameter: About 2.5 mm. Strength: Flexible, but strong. Color: 144A to 144B.

*Reproductive organs.*—Stamens: Quantity per flower, single flowers: About 140. Quantity per flower, semi-double flowers: About 20. Anther shape: Oblong. Anther size: About 6 mm by 1 mm. Anther color: 154B becoming 160A to 160B with development. Amount of pollen: Scarce. Pollen color: Yellow green, close to 154B. Pistils: Quantity per flower, single flowers: About 100. Quantity per flower, semi-double flowers: About 20. Pistil length: About 1.2 cm. Stigma shape: Narrowly conical. Stigma color: Close to 155A. Style length: About 1.1 cm. Style color: 163A. Ovary color: 144A.

*Fruit.*—Quantity per plant: About 2000. Type: Achene. Length: About 3.5 cm. Diameter: About 2 cm. Color: Dark grayish brown.

*Seed.*—Length: About 4 mm. Diameter: About 2 mm. Color: Dark grayish brown.

Disease/pest resistance: Plants of the new Clematis have not been noted to be resistant to pathogens and pests common to Clematis.

Weather tolerance: Plants of the new Clematis have been observed to be tolerant to rain and wind and tolerant to temperatures from 1 to 35° C.

It is claimed:

1. A new and distinct cultivar of Clematis plant named 'Prinsesse Alexandra', as illustrated and described.

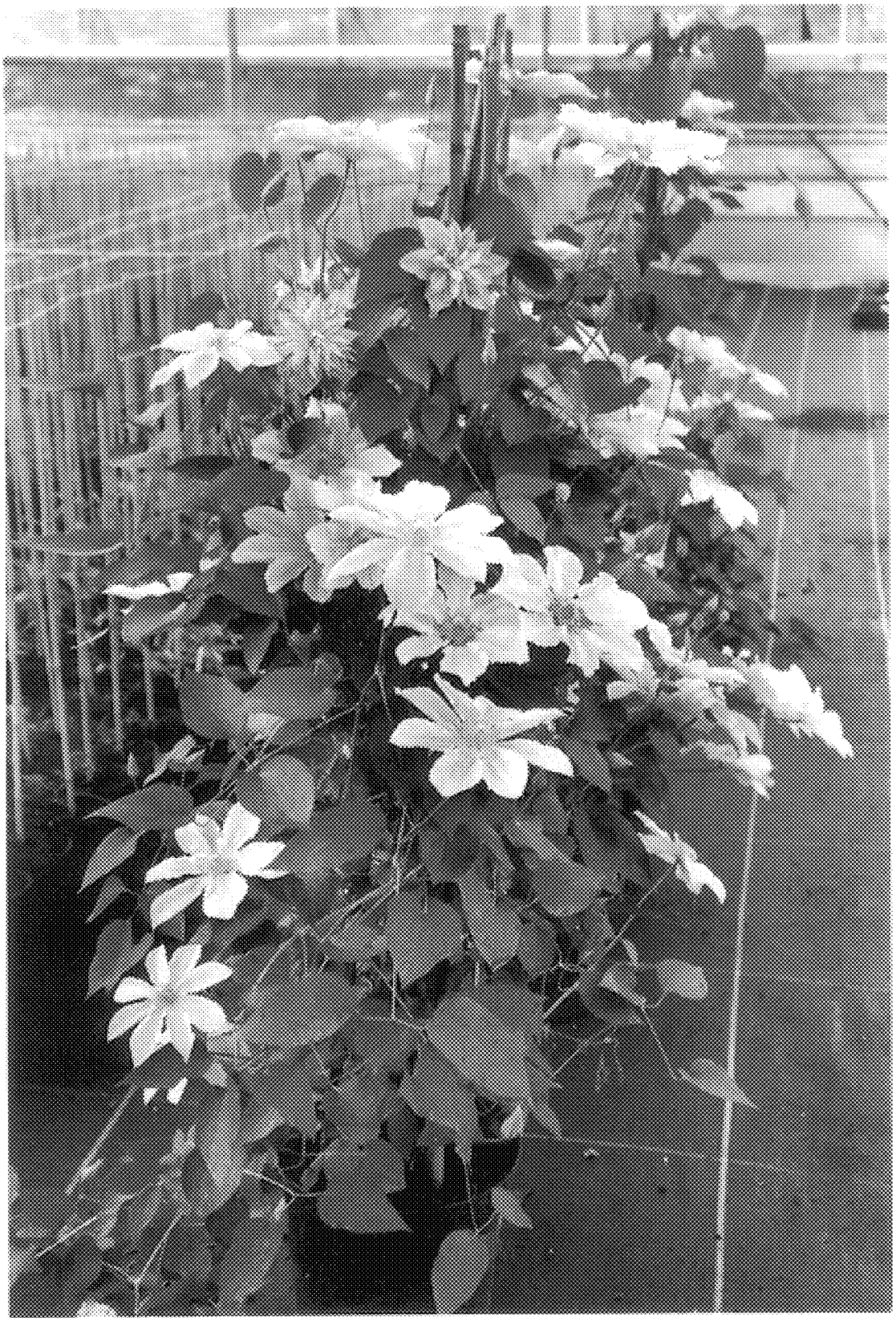

* * * * *